(12) United States Patent  
Aloni et al.

(10) Patent No.: US 8,739,808 B2
(45) Date of Patent: Jun. 3, 2014

(54) PROGRAMMABLE STEAM TRAP APPARATUS

(75) Inventors: Yehoshua Aloni, Kochav Yair-Zur Yigal (IL); Oren Fahimipoor, Tel Aviv (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 894 days.

(21) Appl. No.: 12/800,589

(22) Filed: May 18, 2010

(65) Prior Publication Data

US 2010/0294377 A1 Nov. 25, 2010

Related U.S. Application Data

(60) Provisional application No. 61/216,602, filed on May 19, 2009.

(51) Int. Cl.
*F17D 1/08* (2006.01)

(52) U.S. Cl.
USPC .............. 137/14; 137/171; 137/241; 137/468

(58) Field of Classification Search
USPC ................... 137/14, 171, 203, 468, 238, 241; 236/53–60
See application file for complete search history.

(56) References Cited

U.S. PATENT DOCUMENTS

| | | | |
|---|---|---|---|
| 834,991 A | 11/1906 | McElroy | |
| 3,905,385 A * | 9/1975 | Green | 137/187 |
| 4,261,382 A * | 4/1981 | Bridges | 137/187 |
| 4,372,916 A | 2/1983 | Chamberlain et al. | |
| 4,395,383 A | 7/1983 | Kackos | |
| 4,646,965 A | 3/1987 | Anderson et al. | |
| 4,687,635 A * | 8/1987 | Kaehler et al. | 422/110 |
| 4,705,212 A | 11/1987 | Miller et al. | |
| 4,788,849 A | 12/1988 | Yonemura et al. | |
| 4,813,283 A * | 3/1989 | Craubner | 73/436 |
| 4,830,277 A | 5/1989 | Hood | |
| 4,872,974 A | 10/1989 | Hirayama et al. | |
| 4,898,022 A | 2/1990 | Yumoto et al. | |
| 4,971,764 A * | 11/1990 | Albright | 422/110 |
| 5,196,165 A | 3/1993 | Harrell et al. | |

(Continued)

FOREIGN PATENT DOCUMENTS

| | | |
|---|---|---|
| EP | 0177119 A2 | 4/1986 |
| WO | WO 00/78365 | 12/2000 |

(Continued)

OTHER PUBLICATIONS

PCT International Search Report issued on Jan. 14, 2009 in connection with PCT/US2008/013001, filed Nov. 21, 2008.

(Continued)

*Primary Examiner* — Craig Schneider
*Assistant Examiner* — Craig J Price
(74) *Attorney, Agent, or Firm* — John P. White; Gary J. Gershik; Cooper & Dunham LLP (57) ABSTRACT

An apparatus and a method for removing condensate and unwanted gas from vapor/liquid systems while preventing steam loss are provided. The steam trap apparatus replaces the automatic valve type steam trap with an efficient, controllable, and programmable steam trap. In addition, the improved steam trap apparatus allows for real-time data collection during sterilization and other operations.

19 Claims, 5 Drawing Sheets

(56) References Cited

U.S. PATENT DOCUMENTS

| | | | |
|---|---|---|---|
| 5,478,012 | A | 12/1995 | Fujiwara et al. |
| 5,512,249 | A | 4/1996 | Singh |
| 5,549,134 | A | 8/1996 | Browne et al. |
| 5,623,990 | A | 4/1997 | Pirkle |
| 5,687,755 | A | 11/1997 | Farquhar et al. |
| 6,145,529 | A | 11/2000 | Hellman et al. |
| 6,220,519 | B1 | 4/2001 | Page, Jr. et al. |
| 6,279,593 | B1 | 8/2001 | Sheppard |
| 6,453,802 | B1 | 9/2002 | Manganiello et al. |
| 6,571,180 | B1 | 5/2003 | Turner et al. |
| 6,644,131 | B2 | 11/2003 | Rebik et al. |
| 6,644,132 | B1 | 11/2003 | Baumoel |
| 6,688,329 | B2 | 2/2004 | Murray et al. |
| 7,246,036 | B2 | 7/2007 | Cheskaty et al. |
| 2003/0195472 | A1* | 10/2003 | Green et al. ............. 604/167.04 |
| 2004/0211569 | A1 | 10/2004 | Vinegar et al. |
| 2006/0110280 | A1 | 5/2006 | Nelson et al. |
| 2006/0137817 | A1 | 6/2006 | Ma et al. |
| 2008/0237278 | A1 | 10/2008 | Gaus et al. |
| 2008/0270047 | A1 | 10/2008 | Quake et al. |
| 2009/0199907 | A1 | 8/2009 | Aloni |

FOREIGN PATENT DOCUMENTS

| | | |
|---|---|---|
| WO | WO/2007/038072 | 4/2007 |
| WO | WO/2009/067246 | 5/2009 |
| WO | WO 2010/134977 A1 | 11/2010 |

OTHER PUBLICATIONS

PCT International Search Report issued on Jul. 21, 2010 in connection with PCT/US2010/01466, filed May 18, 2010.
Written Opinion of the International Searching Authority issued on Jan. 14, 2009 in connection with PCT/US2008/013001, filed Nov. 21, 2008.
Written Opinion of the International Searching Authority issued on Jul. 21, 2010 in connection with PCT/US2010/01466, filed May 18, 2010.
International Preliminary Report on Patentability dated May 25, 2010 in connection with International Application No. PCT/US08/013001.
Spirax Sparco USA. "Steam Traps . . . " Spirax Sarco. 2010. http://spiraxsarco.com/resources/steam-engineering-tutorials/steam-traps-and-steam-trapping.asp. Retrieved Jun. 29, 2010.
International Preliminary Report on Patentability dated Nov. 22, 2011 in connection with PCT International Application No. PCTIUS2010/001466, filed May 18, 2010.
Oct. 18, 2011 Office Action issued in connection with U.S. Appl. No. 12/313,563.
Nov. 21, 2011 Office Action issued in connection with U.S. Appl. No. 12/313,563.
Feb. 14, 2012 Amendment in connection with U.S. Appl. No. 12/313,563.
May 18, 2012 Office Action Summary issued in connection with U.S. Appl. No. 12/313,563.
Aug. 17, 2012 Amendment in connection with U.S. Appl. No. 12/313,563.
Nov. 5, 2012 Final Office Action issued in connection with U.S. Appl. No. 12/313,563.
Jan. 4, 2013 Amendment in connection with U.S. Appl. No. 12/313,563.
Jan. 16, 2013 Advisory Action in connection with U.S. Appl. No. 12/313,563.
Apr. 3, 2013 Office Action issued in connection with U.S. Appl. No. 12/313,563.
European Search Report issued Jun. 12, 2013 in connection with European patent application No. EP10778041.3.
Official Action issued Jun. 26, 2013 in connection with European patent application No. EP10778041.3.
Jul. 2, 2013 Amendment submitted in connection with U.S. Appl. No. 12/313,563.
Oct. 7, 2013 Notice of Allowance issued in connection with U.S. Appl. No. 12/313,563.
Oct. 25, 2013 Amendment submitted in connection with European patent application No. EP10778041.3.

* cited by examiner

PROGRAMMABLE STEAM TRAP APPARATUS

This application claims the benefit of U.S. Provisional Application No. 61/216,602, filed May 19, 2009, the entire content of which is hereby incorporated by reference herein.

Throughout this application various publications and published patents are referenced. The disclosures of these publications in their entireties are hereby incorporated by reference into this application in order to more fully describe the state of the art to which this invention pertains.

TECHNICAL FIELD

This application relates to apparatuses, methods, and systems for removing condensate, air, and non-condensable gas from steam space while preventing the loss of steam. In particular, this application relates to an improved steam trap apparatus.

BACKGROUND OF THE INVENTION

In industry, steam, the vaporized form of water, is often used as a repository of energy due to water's high heat of vaporization. Energy is introduced and extracted by heat transfer, and transported in the form of steam from one area of a manufacturing plant to another through pipes.

Steam trap apparatuses are necessary elements of any steam system because they allow steam to reach its destination in as dry a state as possible to perform its task efficiently and economically. Steam trap apparatuses release condensate, air, and non-condensable gas from a steam space while preventing the loss of steam.

Inadequate steam trapping can lead to various undesirable results from steam system inefficiency to waterhammer, corrosion, leakage, and high maintenance costs.

U.S. Pat. Nos. 4,646,965, 4,830,277, 4,898,022, 5,478,012, 6,220,519, 6,279,593, 6,453,802, 6,571,180, and 6,644,131 disclose apparatus and methodologies which can be used to remove condensate and other unwanted gas from steam systems and which are incorporated by reference herein in their entireties.

The conventional steam trap apparatus is comprised of two actuated valves, piping, and a steam trap which is typically an automatic valve not connected to a control system. One actuated valve is situated upstream from the steam trap while the other is positioned in a bypass line upstream from the first actuated valve. The two actuated valves provide a bypass mechanism which is needed for the cleaning of the steam trap apparatus. The outlet of the steam trap and the bypass valve can lead to a condensate return system which re-heats the condensate to form steam or to a drain.

Steam traps are generally of three types: thermostatic, mechanical, and kinematic; each of which contains a number of specific styles.

Thermostatic steam traps are operated by sensing changes in temperature of a fluid, which by definition can include liquids and gases. Three typical types of thermostatic steam traps are the "liquid expansion traps", the "bimetallic traps", and the "balanced pressure thermostatic traps". Thermostatic steam traps may be a misnomer as these steam traps open and close by mechanical operations. An operating element which is responsive to temperature "changes within the desired range is built into the valve so that when the necessary temperature is reached, they react in a way to block the passage of steam to the outlet.

Mechanical steam traps are operated by sensing changes in fluid density. These steam traps operate by sensing the difference in density between steam and condensate. These steam traps include the "ball float traps" and the "inverted bucket traps". In a ball float trap, the ball rises in the presence of condensate, opening a valve which passes the denser condensate. In an inverted bucket trap, the inverted bucket floats when steam reaches the trap and rises to shut the valve.

Kinematic steam traps, sometimes called thermodynamic steam traps, are operated by sensing changes in fluid dynamics. These steam traps rely partly on the formation of flash steam from condensate. This group includes the "thermodynamic", the "disc", the "impulse" and the "labyrinth" steam traps.

The three types of steam traps are more comprehensively described in industry catalogues such as the Spirax Sarco steam trap catalogue which can be found at the following web address: spiraxsarco.com/resources/steam-engineering-tutorials/steam-traps-and-steam-trapping.asp.

SUMMARY OF THE INVENTION

The subject application provides an apparatus for removing condensate, air, or non-condensable gas from vapor space in a vapor system while preventing the loss of vapor, the apparatus comprising a first temperature sensor, a second temperature sensor, at a position in the vapor system where condensate, air, or non-condensable gas collect, and which position is different from the position of the first temperature sensor, a pressure sensor, an actuated valve in a position allowing for the release of condensate, air, or non-condensable gas from the vapor space, and a control system which receives output from the first and second temperature sensors and from the pressure sensor and determines whether to open the actuated valve to release condensate, air or non-condensable gas from the vapor space based on temperature reading from the temperature sensors and the pressure reading from the pressure sensor.

The subject application also provides a method for removing condensate, air, or non-condensable gas from vapor space in a vapor system while preventing the loss of vapor, the method comprising: a) measuring the temperature at a first region in the vapor system; b) measuring the temperature at second region in the vapor system where condensate, air, or non-condensable gas collect, wherein the second region is different from the first region; c) measuring the pressure at a region in the vapor system; d) determining whether the temperatures and pressure obtained in steps a)-c) represents the presence of condensate, air, or non-condensable gas; and e) opening an actuated valve if the temperatures and pressure measured in steps a)-c) is determined to represent presence of condensate, air, or non-condensable gas.

The subject application also provides a steam trap apparatus for removing condensate, air, or non-condensable gas from steam space in a steam system while preventing the loss of steam, the apparatus comprising: a first temperature sensor, a second temperature sensor, at a position in the steam system where condensate, air, or non-condensable gas collect, and which position is different from the position of the first temperature sensor, a pressure sensor, an actuated valve in a position allowing for the release of condensate, air, or non-condensable gas from the steam space, and a control system which receives output from the first and second temperature sensors and from the pressure sensor and determines whether to open the actuated valve to release condensate, air or non-condensable gas from the steam space based on temperature reading from the temperature sensors and the pressure reading from the pressure sensor.

The subject application also provides a method for removing condensate, air, or non-condensable gas from steam space in a steam system while preventing the loss of steam, the method comprising: a) measuring the temperature at a first region in the steam system; b) measuring the temperature at a second region in the steam system where condensate, air, or non-condensable gas collect, wherein the second region is different from the first region; c) measuring the pressure at a region in the steam system; d) determining whether the temperatures and pressures obtained in steps a)-c) represents the presence of condensate, air, or non-condensable gas; and e) opening an actuated valve if the temperatures and pressure measured in steps a)-c) is determined to represent presence of condensate, air, or non-condensable gas.

BRIEF DESCRIPTION OF THE DRAWINGS

The features of the present application can be more readily understood from the following detailed description with reference to the accompanying drawings wherein.

DETAILED DESCRIPTION

Embodiments of the Invention

The subject application provides an apparatus for removing condensate, air, or non-condensable gas from vapor space in a vapor system while preventing the loss of vapor, the apparatus comprising a first temperature sensor, a second temperature sensor, at a position in the vapor system where condensate, air, or non-condensable gas collect, and which position is different from the position of the first temperature sensor, a pressure sensor, an actuated valve in a position allowing for the release of condensate, air, or non-condensable gas from the vapor space, and a control system which receives output from the first and second temperature sensors and from the pressure sensor and determines whether to open the actuated valve to release condensate, air or non-condensable gas from the vapor space based on temperature reading from the temperature sensors and the pressure reading from the pressure sensor.

In one embodiment, the actuated valve is a sanitary valve. In another embodiment, the actuated valve is a valve other than a sanitary valve. In another embodiment, the actuator for the actuated valve is mechanical, electrical, electromechanical, pneumatic, or human.

In one embodiment, the temperature sensors are thermometers, thermocouples, temperature sensitive resistors such as a thermistors or resistance temperature detectors, bimetal thermometers, or thermostats.

In one embodiment, the first temperature sensor is located directly in the pipes or a vessel in the vapor system. In another embodiment, the second temperature sensor is located directly in the pipes or the actuated valve. In another embodiment, one or both of the temperature sensors are located within a thermowell pocket. In yet another embodiment, the thermowell pocket further comprises glycerol.

In one embodiment, the actuated valve is positioned downstream from the first and the second temperature sensors.

In one embodiment, the control system opens the actuated valve if it determines that condensate, air or non-condensable gas is present in the vapor system. In another embodiment, the control system determines that condensate, air or non-condensable gas is present in the vapor system if the outputs from the temperature sensors and from the pressure sensor indicate that the vapor system is operating at below the saturation curve of the vapor.

In one embodiment, the control system is programmed to allow input of time intervals which represent the time delay between a signal to open or close the actuated valve and the opening or closing of the actuated valve.

In one embodiment, the distance between the vapor space and the actuated valve is 20 meters or less. In another embodiment, the distance between the vapor space and the actuated valve is 80 cm or less. In another embodiment, the distance between the vapor space and the actuated valve is 5 cm or less.

In one embodiment, the pressure in the vapor space is 1-5 bar. In another embodiment, the pressure in the vapor space is between 2-3 bar. In another embodiment, the pressure in the vapor space is between 1-2 bar.

In one embodiment, the apparatus further comprises a second actuated valve. In another embodiment, the second actuated valve controls vapor supply to the apparatus. In yet another embodiment, the second actuated valve is actuated by an output from the control system.

The subject application also provides a method for removing condensate, air, or non-condensable gas from vapor space in a vapor system while preventing the loss of vapor, the method comprising: a) measuring the temperature at a first region in the vapor system; b) measuring the temperature at second region in the vapor system where condensate, air, or non-condensable gas collect, wherein the second region is different from the first region; c) measuring the pressure at a region in the vapor system; d) determining whether the temperatures and pressure obtained in steps a)-c) represents the presence of condensate, air, or non-condensable gas; and e) opening an actuated valve if the temperatures and pressure measured in steps a)-c) is determined to represent presence of condensate, air, or non-condensable gas.

In one embodiment, the actuated valve is a sanitary valve. In another embodiment, the actuated valve is a valve other than a sanitary valve.

In another embodiment, the temperature obtained in step a) is obtained directly from within the pipes or a vessel in the vapor system. In another embodiment, the temperature obtained in step b) is obtained directly from within the pipes or the actuated valve. In another embodiment, the temperature obtained in step a) or b) or both is obtained from within a thermowell pocket. In yet another embodiment, the thermowell pocket further comprises glycerol.

In one embodiment, the determining step in d) is accomplished by comparing the temperatures and pressure obtained in steps a)-c) with the saturation curve of the vapor. In another embodiment, the actuated valve is opened if the temperatures and pressure obtained in steps a)-c) indicate that the vapor system is operating at below the saturation curve of the vapor. In another embodiment, the determining step in d) is automated. In yet another embodiment, the automation is achieved by a control system.

In one embodiment, the control system is programmed to allow input of time intervals which represent the time delay between a signal to open or close the actuated valve and the opening or closing of the actuated valve. In another embodiment, the actuated valve opening time interval is no more than 20 seconds. In another embodiment, the actuated valve opening time interval is 1-10 seconds.

In one embodiment, the distance between the vapor space and the actuated valve is 20 meters or less. In another embodiment, the distance between the vapor space and the actuated valve is 80 cm or less. In another embodiment, the distance between the vapor space and the actuated valve is 5 cm or less.

In one embodiment, the pressure in the vapor space is 1-5 bar. In another embodiment, the pressure in the vapor space is 2-3 bar. In another embodiment, the pressure in the vapor space is 1-2 bar.

The subject application also provides a steam trap apparatus for removing condensate, air, or non-condensable gas from steam space in a steam system while preventing the loss of steam, the apparatus comprising: a first temperature sensor, a second temperature sensor, at a position in the steam system where condensate, air, or non-condensable gas collect, and which position is different from the position of the first temperature sensor, a pressure sensor, an actuated valve in a position allowing for the release of condensate, air, or non-condensable gas from the steam space, and a control system which receives output from the first and second temperature sensors and from the pressure sensor and determines whether to open the actuated valve to release condensate, air or non-condensable gas from the steam space based on temperature reading from the temperature sensors and the pressure reading from the pressure sensor.

In one embodiment, the actuated valve is a sanitary valve. In another embodiment, the actuated valve is a valve other than a sanitary valve. In another embodiment, the actuator for the actuated valve is mechanical, electrical, electromechanical, pneumatic, or human.

In one embodiment, the temperature sensors are thermometers, thermocouples, temperature sensitive resistors such as a thermistors or resistance temperature detectors, bimetal thermometers, or thermostats.

In one embodiment, the first temperature sensor is located directly in the pipes or a vessel in the steam system. In another embodiment, the second temperature sensor is located directly in the pipes or the actuated valve. In another embodiment, one or both of the temperature sensors are located within a thermowell pocket. In yet another embodiment, the thermowell pocket further comprises glycerol.

In one embodiment, the actuated valve is positioned downstream from the first and the second temperature sensors.

In one embodiment, the control system opens the actuated valve if it determines that condensate, air or non-condensable gas is present in the steam system. In another embodiment, the control system determines that condensate, air or non-condensable gas is present in the steam system if the outputs from the temperature sensors and from the pressure sensor indicate that the steam system is operating at below the steam saturation curve.

In one embodiment, the control system is programmed to allow input of time intervals which represent the time delay between a signal to open or close the actuated valve and the opening or closing of the actuated valve.

In one embodiment, the distance between the steam space and the actuated valve is 20 meters or less. In another embodiment, the distance between the steam space and the actuated valve is 5 cm or less. In another embodiment, the distance between the steam space and the actuated valve is 5 cm or less.

In one embodiment, the pressure in the steam space is 1-5 bar. In another embodiment, the pressure in the steam space is between 2-3 bar. In another embodiment, the pressure in the steam space is between 1-2 bar.

In one embodiment, the apparatus further comprises a second actuated valve. In another embodiment, the second actuated valve controls steam supply to the apparatus. In yet another embodiment, the second actuated valve is actuated by an output from the control system.

The subject application also provides a method for removing condensate, air, or non-condensable gas from steam space in a steam system while preventing the loss of steam, the method comprising: a) measuring the temperature at a first region in the steam system; b) measuring the temperature at a second region in the steam system where condensate, air, or non-condensable gas collect, wherein the second region is different from the first region; c) measuring the pressure at a region in the steam system; d) determining whether the temperatures and pressures obtained in steps a)-c) represents the presence of condensate, air, or non-condensable gas; and e) opening an actuated valve if the temperatures and pressure measured in steps a)-c) is determined to represent presence of condensate, air, or non-condensable gas.

In one embodiment, the actuated valve is a sanitary valve. In another embodiment, the actuated valve is a valve other than a sanitary valve.

In another embodiment, the temperature obtained in step a) is obtained directly from within the pipes or a vessel in the steam system. In another embodiment, the temperature obtained in step b) is obtained directly from within the pipes or the actuated valve. In another embodiment, the temperature obtained in step a) or b) or both is obtained from within a thermowell pocket. In yet another embodiment, the thermowell pocket further comprises glycerol.

In one embodiment, the determining step in d) is accomplished by comparing the temperatures and pressure obtained in steps a)-c) with the steam saturation curve. In another embodiment, the actuated valve is opened if the temperatures and pressure obtained in steps a)-c) indicate that the steam system is operating at below the steam saturation curve. In another embodiment, the determining step in d) is automated. In yet another embodiment, the automation is achieved by a control system.

In one embodiment, the control system is programmed to allow input of time intervals which represent the time delay between a signal to open or close the actuated valve and the opening or closing of the actuated valve. In another embodiment, the actuated valve opening time interval is no more than 20 seconds. In another embodiment, the actuated valve opening time interval is 1-10 seconds.

In one embodiment the distance between the steam space and the actuated valve is 20 meters or less. In another embodiment, the distance between the steam space and the actuated valve is 80 cm or less. In another embodiment, the distance between the steam space and the actuated valve is 5 cm or less.

In one embodiment, the pressure in the steam space is 1-5 bar. In another embodiment, the pressure in the steam space is 2-3 bar. In another embodiment, the pressure in the steam space is 1-2 bar.

All combinations of the various elements described herein are within the scope of the invention.

It is understood that where a parameter range is provided, all integers within that range, and tenths thereof, are also provided by the invention. For example, "1-5 bar" includes 1.0, 1.1, 1.2, 1.3, 1.4 etc. up to 5.0 bar.

Terms

For the purposes of this application:

The term "vapor" means the gaseous phase of any material.

The term "vapor system" means the combination of equipment which are connected for the purposes of transporting and cycling fluid matter, whether in the form of condensate or vapor, and the maintenance thereof, which can include but is not limited to a boiler, feed system, pumps, piping, valves, condensate return system, and drain.

The term "vapor space" means the portion of a vapor system where vapor is contained, which can include but is not limited to the interior of pipes, vessels, or other types of container and equipment.

The term "steam system" means the combination of equipment which are connected for the purposes of transporting and cycling water, whether in the form of condensate or steam, and the maintenance thereof, which can include but is not limited to a boiler or steam generating unit, feedwater system, pumps, piping, valves, condensate return system, and drain.

The term "steam space" means the portion of a steam system where steam is contained, which can include but is not limited to the interior of pipes, vessels, or other types of container and equipment.

The term "saturation curve" with respect to a vapor is the graph of saturation temperatures of the vapor material at various pressures. The saturation temperature is the temperature at which the material in its liquid phase boils into its vapor phase for a given pressure. The liquid can be said to be saturated with thermal energy. Any addition of thermal energy results in a phase change. If a vapor system is operating at above its saturation curve, the vapor is superheated. If a vapor system is operating at below its saturation curve, the vapor condenses to its liquid phase. If a vapor system is operating at its saturation curve, the gaseous phase and the liquid phase of the vapor material coexist, both being at the saturation temperature.

The term "actuated valve" means a valve which is controlled by some outside force, be it manual, pneumatic or electronic. Actuated valves specifically exclude the three common known types of steam traps, the thermostatic, the mechanic, and the kinetic steam trap.

The term "sanitary valve" means a diaphragm or membrane or any other type of cleanable valve which is designed for use in applications requiring clean or sterile processing and is constructed using compliant materials that can withstand sanitizing and sterilizing methods.

The term "thermowell" means the instruments used in industrial temperature measurement to provide isolation between a temperature sensor and the environment whose temperature is to be measured.

The term "control system" means a device or set of devices which regulates the behavior of other devices or systems. In one embodiment, it can be a computer which automatically or with user interface controls other devices via electronic signals or wireless signals.

The term "temperature sensor" means a device or set of devices which obtain information for temperature measurement, and which may be connected to send the data to another control device.

The term "pressure sensor" means a device or set of devices which obtain information for pressure measurement, and which may be connected to send the data to another control device.

The Problem with the Conventional Steam Traps

There are multiple problems with the conventional steam trap apparatuses and steam traps.

First, the conventional steam traps are without capability to be re-set or controlled once installed. This is because the operation of an automatic valve is purely mechanical. For example, a typical embodiment of a thermostatic steam trap is the bimetallic steam trap. The operating element of a bimetallic steam trap is a bimetallic disk constructed using two strips of dissimilar metals welded together. The element deflects when heated, thereby blocking the passage of steam to the condensate return line or drain.

However, temperature is not the only parameter which affects the formation of steam. Other operating conditions such as pressure (P) and load (V) affects the vaporization of water. When load is fixed, water vaporizes according to a steam saturation curve; the higher the pressure in the system, the higher the saturation temperature of steam. The steam saturation curve is a concave arc. On the other hand, the operating curve of a bimetallic steam trap is essentially linear due to the slow response of metals to changing conditions.

Furthermore, it is possible that the steam trap operating temperature is actually above the steam saturation temperature at low pressures. As a result, the steam trap would release steam at these lower pressures, causing steam loss. It may be possible to manufacture the steam trap to ensure that this portion of the saturation curve is always above the operating curve. However, due to the linear action of the element, the difference between the two lines would increase even more with system pressure, increasing the waterlogging effect, where condensate collects and the valve remains closed, preventing condensate drain.

More innovative bimetallic steam traps use multiple layers of metal. In multi-layer bimetallic steam traps, different layers of bimetal disks are used so that one set of bimetal element deflects to give response to one pressure range. At a higher temperature, a second set of bimetal element contributes to give response to a different pressure range. In this way, the operating curve of the steam trap can be manipulated to more closely resemble the steam saturation curve. Though an improvement on the former design, the operating curve of this steam trap still does not exactly replicate the steam saturation curve, which is desirable for efficient operation of the steam trap apparatus.

Other automatic-valve-type steam traps similarly suffer from inflexibility in response to varying operating conditions.

There is a need for improvements to the techniques and apparatuses for steam trapping to increase efficiency, flexibility, controllability, and simplicity.

The Programmable Steam Trap (PST)

This disclosure describes improvements to methodologies and apparatuses for removing condensate and unwanted gas from the steam space in a steam system while preventing steam loss. The improved methodology and apparatus is simpler, more efficient and more flexible than the existing steam trapping apparatuses, is highly programmable and controllable, and allows for real-time data collection. This disclosure includes improvements to methodologies and apparatuses for removing condensate and unwanted gas from the vapor space in any vapor system while preventing vapor loss.

Exemplary embodiments of the present invention will be explained below while referring to the accompanying drawings.

Figure 1:
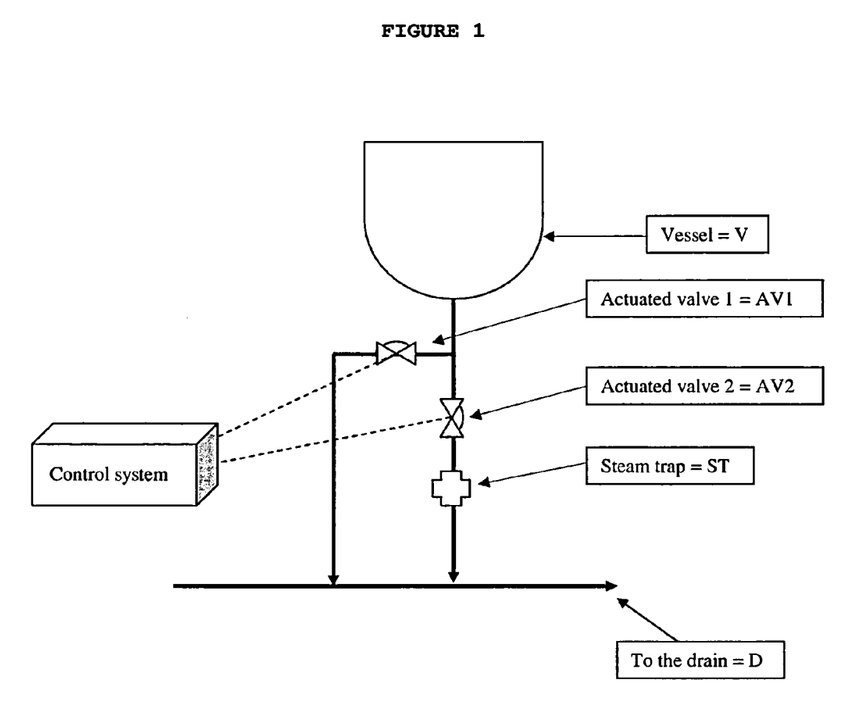
FIG. 1: shows a schematic diagram of a conventional steam trap apparatus.
Figure 2:
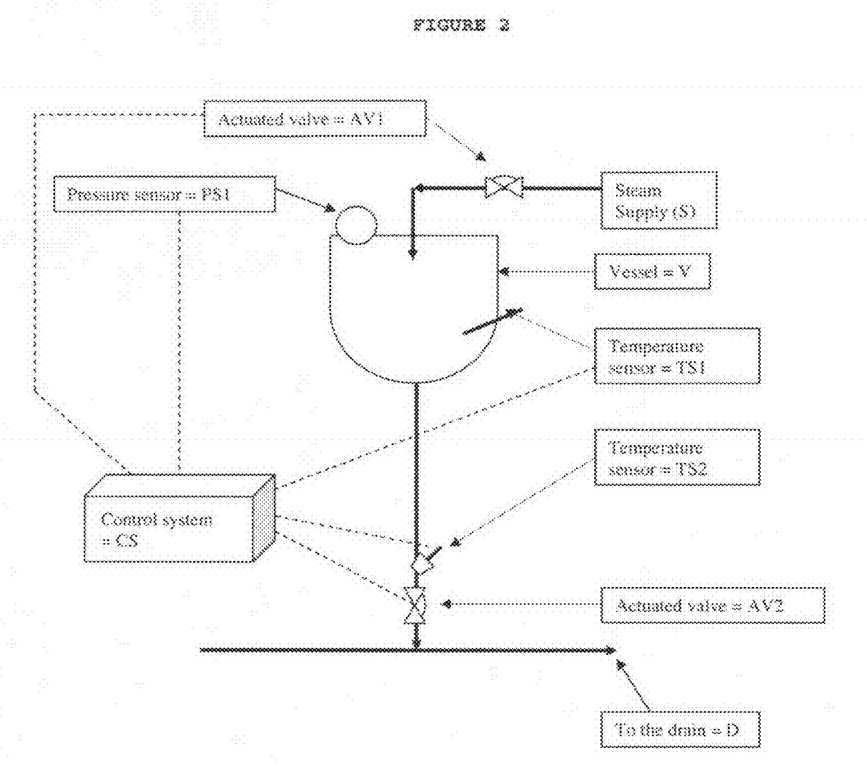
FIG. 2: shows the schematic diagram of the Programmable Steam Trap apparatus (PST) set up for Experiment 1.

FIG. 1 shows a schematic diagram of a conventional steam trap apparatus, including a bypass line; FIG. 2 shows a schematic diagram of a steam trap apparatus according to an exemplary embodiment of this application.

A Programmable Steam Trap apparatus (PST) for removing condensate and unwanted gas from a steam system while preventing steam loss will be described with reference to FIG.

2. The apparatus allows condensate and other unwanted gas to be separated from the steam system so that the steam in the steam system can reach its destination in as dry a state as possible to perform its task efficiently and economically.

In one embodiment of this application, the improved steam trap apparatus comprises an actuated valve positioned at a point in the steam system where condensate, air, and non-condensable gases are likely to gather (AV2). The apparatus further comprises two electronically controlled temperature sensors, each with a transmitter, one positioned near or in the actuated valve (TS2), and the other positioned upstream from TS2 (TS1). The apparatus also comprises a pressure sensor positioned upstream from AV2 and TS2 (PS1).

Figure 4:
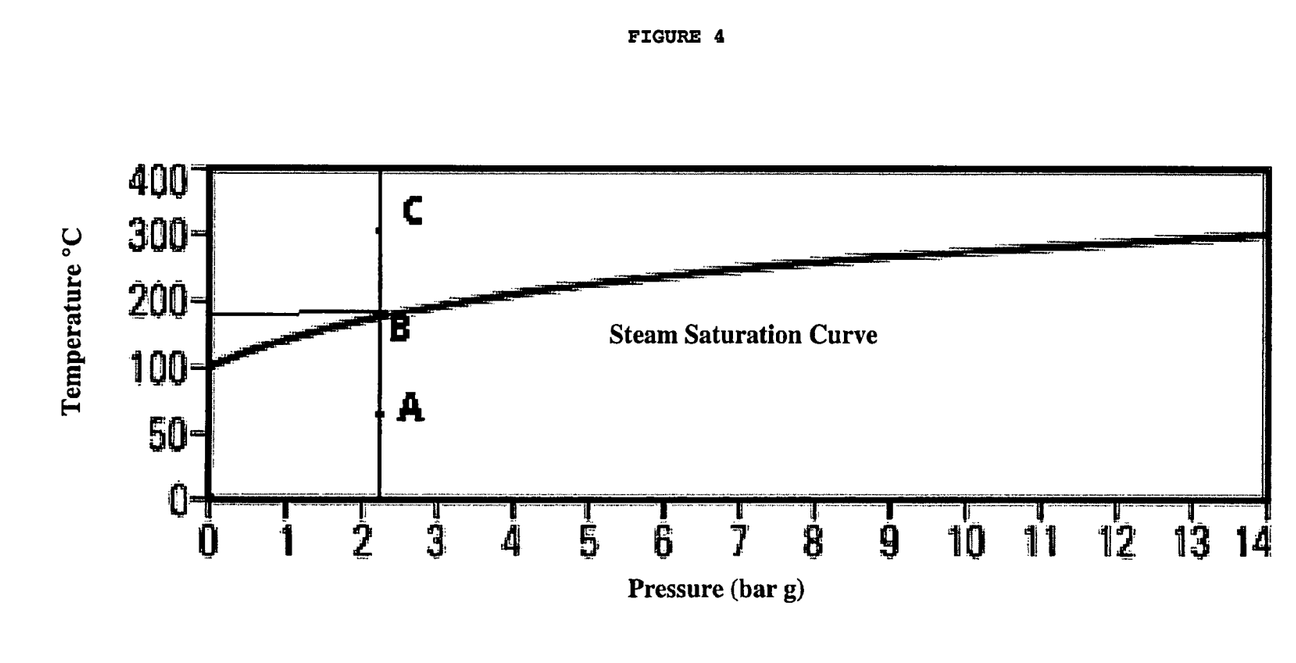
FIG. 4: shows the steam saturation curve.

In this setup, the temperature and pressure sensors detect the temperature and pressure in their respective areas and send corresponding outputs to a control system. The control system determines whether condensate, air, and non-condensable gases are present in the system by comparing the output from the temperature and pressure sensors (TS1 and PS1) to the saturation curve of the vapor. Where the vapor is steam, the control system compares the output from the temperature pressure sensors to the steam saturation curve (FIG. 4). The control system then sends an output to the actuated valve (AV2) to open to release condensate, or to close to retain vapor or steam. TS2 can be positioned near the AV2 valve or in the valve itself. FIG. 2 shows the TS2 located near AV2 inside a thermowell. In an embodiment of the present invention, the thermowell can further comprise glycerol.

In addition, the Programmable Steam Trap apparatus can be optimized to accommodate a range of steam or vapor systems. For example, it may be desirable to program the control system to allow input of time intervals which represent the time delay between a signal to open or close the actuated valve and the opening or closing of the actuated valve. The time interval can be limited to no more than 2 seconds, or no more than 1 second. The time interval can also be 1-10 seconds. Also, the distance between the vapor space and the actuated valve can vary. The pipe length between the vapor space and the actuated valve can be, for example, 5 cm or less, 100 cm or less, 10 meters or less or more than 10 meters.

The improved steam trap apparatus allows for more flexible and efficient operation because it is responsive to varying operating conditions. The apparatus which can accommodate a steam or vapor system operating at atmospheric pressure can also accommodate a steam or vapor system operating at elevated pressures at between 2 and 3 bar, at up to 2.25 bar, up to 2.5 bar or more. Also, the improved steam trap apparatus is highly programmable and controllable, and allows for real-time data to be collected (such as temperature, pressure and valve position) during operation, cleaning, or sterilization.

A saturation curve indicates the saturation temperature of a given liquid at various pressures. The saturation temperature is the temperature at which a liquid boils into its vapor phase for a corresponding saturation pressure. The liquid can be said to be saturated with thermal energy. Any addition of thermal energy results in a phase change. As pressure increases, the saturation temperature increases, but not linearly. On a steam saturation curve, the curve indicates the point at which water and steam can coexist for a given pressure, both being at the saturation temperature. (see FIG. 4)

Ideally, the operating curve of the steam trap should replicate the steam saturation curve, and the valve opens and closes at the exact point of saturation of water, to achieve optimum efficiency.

In the improved steam trap apparatus, the temperature and pressure which triggers the actuated valve will reflect the actual saturation temperature ($T_{sat}$) and saturation pressure ($P_{sat}$) at the given operating condition. This can be accomplished by programming the saturation points at varying operating parameters into the control system. The saturation temperature and pressure data for common elements such as water can be found in Perry's Chemical Engineers' Handbook, $7^{th}$ ed. Perry and Green, McGraw-Hill Professional; 7 edition (Jun. 1, 1997). This data is incorporated by reference herein.

The control system can obtain other operating parameters such as load by other sensors in the system or by user input. The control system, through an algorithm, then determines the corresponding saturation temperature and pressure for the given operating condition.

In a normal steam operation the temperature setting is $T_{sat}=121°$ C., the saturation temperature of steam at 1 atm, the standard atmospheric pressure and the pressure at earth's sea level. When the steam system temperature is above $T_{sat}$, the steam in the system is dry and the control system closes the actuated valve to prevent steam loss. When the steam system temperature is below $T_{sat}$, the steam in the system has lost heat and became condensate, the control system opens the valve to drain the condensate.

In addition, users can bypass the algorithm which determines $T_{sat}$ to be the triggering point of the actuated valve, and manually re-program the control system to open and close the actuated valve to fit the cleaning needs.

Hence, in one embodiment, the steam trap apparatus operates as follows during the normal steam system operation: the temperature sensors (TS1 and TS2) and the pressure sensor (PS1) send outputs to the control system indicating the temperature and pressure readings at their respective positions. The control system compares the temperature and pressure readings (at TS1 and PS1) to the steam saturation curve. If the temperature and pressure reading correspond to a point which is below steam saturation curve (see FIG. 4), then condensate, air, or non-condensable gas is present in the system. The control system will then send an output to the actuated valve to open and release the condensate, air, or non-condensable gas. As condensate, air, or non-condensable gas are released, the system temperature rises and the system pressure falls. The control system monitors the temperature and pressure readings until they correspond to a point which is on or above the steam saturation curve. When the temperature and pressure readings correspond to a point which is on the steam saturation curve, saturated steam is present. When the temperature and pressure readings correspond to a point which is above the steam saturation curve, superheated steam is present. Therefore, when the temperature and pressure readings correspond to a point which is at or above the steam saturation curve, the control system directs the actuated valve to remain closed to prevent loss of steam.

The above embodiment is described with respect to a steam system. However, the apparatus can operate in the same way for another vapor system.

Sterilization and Cleaning of the Programmable Steam Trap

The pharmaceutical, biopharmaceutical, cosmetics and food industries utilizes equipment made of high grade stainless steel (S.S.), such as fermentors, that are too large or too inconvenient to place in either an autoclave, oven or parts washer for sterilization or cleaning. Sterilization-In-Place ("SIP") is a process for sterilizing such processing equipment. A typical SIP process, which is used to kill microorganisms, mimics an autoclave operation and consists of the following steps: air purge, heating period, sterilization holding period, sterile displacement and collapse of the steam blanket.

SIP is a time-dependent process that should approach a well-defined steady state, corresponding to the sterilization conditions. Sterilization can be accomplished by thermal, chemical, or other methods, but the United States Food and Drug Administration (FDA) (1975) and the European Economic Community (EEC) (1990) state preference for thermal methods. The process generally subjects the equipment(s) to a certain pressure and high temperature for an amount of time. (FDA regulations (1975) require that sterilization meet or be equivalent to the following conditions: 121.5° C. maintained for 20 minutes with saturated steam). Since the typical temperature of sterilization is in the range of 121° C. to 125° C., steam is generally used for SIP purposes.

CIP operation, on the other hand, is the common method to clean process equipments in general. The medium for cleaning is generally a room temperature cleaning liquid, but sometimes a hot cleaning liquid may be required.

Hence, in one embodiment, the SIP process for the PST operates as follows: First, the system pressure at which the sterilization will take place ($P_{sterilization}$) is selected. $P_{sterilization}$ can be programmed into the control system ahead of time or selected by the operator prior to the start of SIP. Then, the control system determines the temperature which corresponds to the $P_{sterilization}$ on the steam saturation curve ($T_{sterilization}$). Alternatively $P_{sterilization}$ can also be determined by the control system based on a $T_{sterilization}$ programmed into the control system ahead of time or selected by the operator prior to the start of SIP.

At the start of SIP, an actuated valve controlling the supply of steam to the PST apparatus ("steam supply valve") is opened to allow steam into to the PST apparatus and to increase pressure. The pressure in PST apparatus is allowed to build gradually, e.g., an increase of 0.5 bar followed by a decrease of 0.25 bar, until $P_{sterilization}$ is reached. This first stage of the SIP process is the "heating stage".

Upon reaching $P_{sterilization}$, the system temperature is monitored. At this point in the SIP process, three options are available:

1. If the temperature is lower than $T_{sterilization}$ by more than −1° C., there is still condensate in the system. An actuated valve which opens to drain (the "drain valve") is opened for several seconds to discharge all the condensate and the "heating stage" continues. At this time the steam supply valve is opened and the pressure in the system is maintained at $P_{sterilization}$.
2. If the temperature is higher than $T_{sterilization}$ by more than 1° C., the system contains superheated steam. The drain valve is opened for several seconds in order to decrease the pressure and the temperature. At this time the steam supply valve is closed.
3. If the temperature is $T_{sterilization}$ ±0.5° C., the system is operating on the steam saturation curve. In this scenario, both the steam supply valve and the drain valve remain closed. As the sterilization progresses, if the pressure rises too high, the drain valve is opened for several seconds. If the pressure falls too low, the drain valve remains closed. The drain valve in this case is controlled according to the temperature at or near the drain valve. In this manner the operation curve the sterilization process remains on or close to the steam saturation curve.

During sterilization of the PST, the system is controlled on line and the temperature is measured on line. The process will continue on the steam saturation curve for 20 minutes, which is the minimum required time for sterilization.

The above embodiment is described with respect to a steam system. However, the apparatus can operate in the same way for another vapor system.

PST is advantageous over the conventional steam trap apparatuses because, during SIP or any operation, real-time data can be collected since the temperature sensors (TS1 and TS2), the pressure sensor (PS1), and the actuated valves (AV1 and AV2) are attached to the control system. (see FIG. 2) As a result, every sterilization cycle is validated and documented.

Moreover, sterilization time is shorter for the PST than for the standard steam trap apparatus. The initial heating period for the system to reach the saturation point is proportional to the load in the PST apparatus, but once the saturation point is reached, sterilization period is only 20 minutes, i.e. the minimum time required for sterilization. Also, PST sterilization minimizes steam loss. Common steam traps may waste up to 20% of the steam. The cost of this loss is estimated to be anywhere from thousands to millions of dollars every year depending on the manufacturing facility. The PST may save 10-50% of the lost steam since significantly less superheated steam is formed. Also, reduced requirement for steam translates into purified water savings and energy savings. Finally, PST allows for sterilization at the minimum allowed sterilization temperature. Operating at the minimum allowed temperature is desirable because this minimizes negative impact on media quality and damage to the system or parts of the system such as electrodes or other sensors. Operating at the minimum allowed sterilization temperature can prevent 5-20% of medium damage and 2-10% of system's parts damage.

Thus, the improved steam trap apparatus disclosed in this application is advantageous over the conventional steam trap apparatus. It is flexible, efficient, and highly controllable since the steam trap itself is an actuated valve attached to a programmable control system.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

Experimental Details

Experiment 1

The steam trap apparatus as shown in FIG. 2 was tested. The apparatus comprises two temperature sensors and a pressure sensor: one temperature sensor (TS2) is located in the actuated valve (AV2) or close to the valve, and the other one (TS1) is located in a vessel (V). The pressure sensor (PS1) is also located in the vessel. Steam is supplied to the vessel via an actuated valve (AV1) and drained through a second actuated valve (AV2).

An external control system receives the input from the temperature and pressure sensors. A set point for the desired sterilization temperature, for example, 122 or 123° C., is entered ($T_{sterilization}$) and the system finds the correlating pressure ($P_{sterilization}$) from the steam saturation curve. Alternatively, a set point for the sterilization pressure ($P_{sterilization}$), for example, 1.3 bar gauge, is entered, and the system finds the correlating temperature ($T_{sterilization}$). As discussed supra, FDA regulations (1975) require that sterilization meet or be equivalent to the following conditions: 121.5° C. maintained for 20 minutes with saturated steam. Therefore, it is preferable that $T_{sterilization}$ chosen be close to the mandated minimum temperature to avoid waste of energy and steam.

The valves (AV1 and AV2) are controlled during sterilization. The control system reads the temperature and pressure periodically (e.g., every second) and sends a signal to the valves (AV1 and AV2) to open or to close accordingly.

Materials and Equipment
1. Steam supply source (S)—5 liter steam generator (BABY ECO, Tecnovap, Italy);
2. Controlled valve for steam supply (AV1)—½"-diameter pneumatic valve (Saunders, available from Crane Process Flow Technologies Ltd., UK);
3. Stainless steel vessel (V) with a PT 100 temperature sensor (TS1) and a pressure sensor (PS1) (Elcon International, Sweden);
4. Drain pipes (D)—½"-diameter and 80 cm long;
5. Pipe with a PT 100 temperature sensor (TS2)—½"-diameter 10 cm (T-pipe);
6. A controlled (actuated) valve in the drain pipe (AV2)—½"-diameter pneumatic valve (Saunders, available from Crane Process Flow Technologies Ltd., UK); and
7. A control system (CS)—Custom PLC (Programmable Logic Controller) made from Biosoft®, Israel and RSview® available from Rockwell Automation, Milwaukee, Wis.

Methods

For the PST apparatus, sterilization can be broken down into two stages: the initial heating stage and the sterilization stage. The sterilization process of the PST is described below with reference to FIG. 2.

The heating stage: Prior to the start of the sterilization process, the system pressure can be at atmospheric pressure (1.01 bar, 0 bar gauge). At the start of the sterilization process, AV1 valve is opened. As steam flows from the steam supply line into to the vessel, the pressure in the vessel rises. When the pressure in the vessel rises by 0.5 bar gauge as indicated by PS1, AV2 is opened to release condensate which accumulates at the bottom of the vessel and to decrease system pressure. Once the pressure in the vessel falls by 0.25 bar gauge, AV2 is again closed to increase system pressure until it rises by another 0.5 bar gauge. At this point AV2 is opened again to decrease the system pressure. The pressure in the vessel is gradually built in this manner, i.e., an increase of 0.5 bar gauge followed by a decrease of 0.25 bar gauge until pressure of the set point (e.g., $P_{sterilization}$=1.3 or 1.5 bar gauge) is reached.

The sterilization stage: Once the system reaches the pressure set point ($P_{sterilization}$) and $T_{sterilization}$ (e.g., 122 or 123° C.), the sterilization stage begins.

Figure 3:
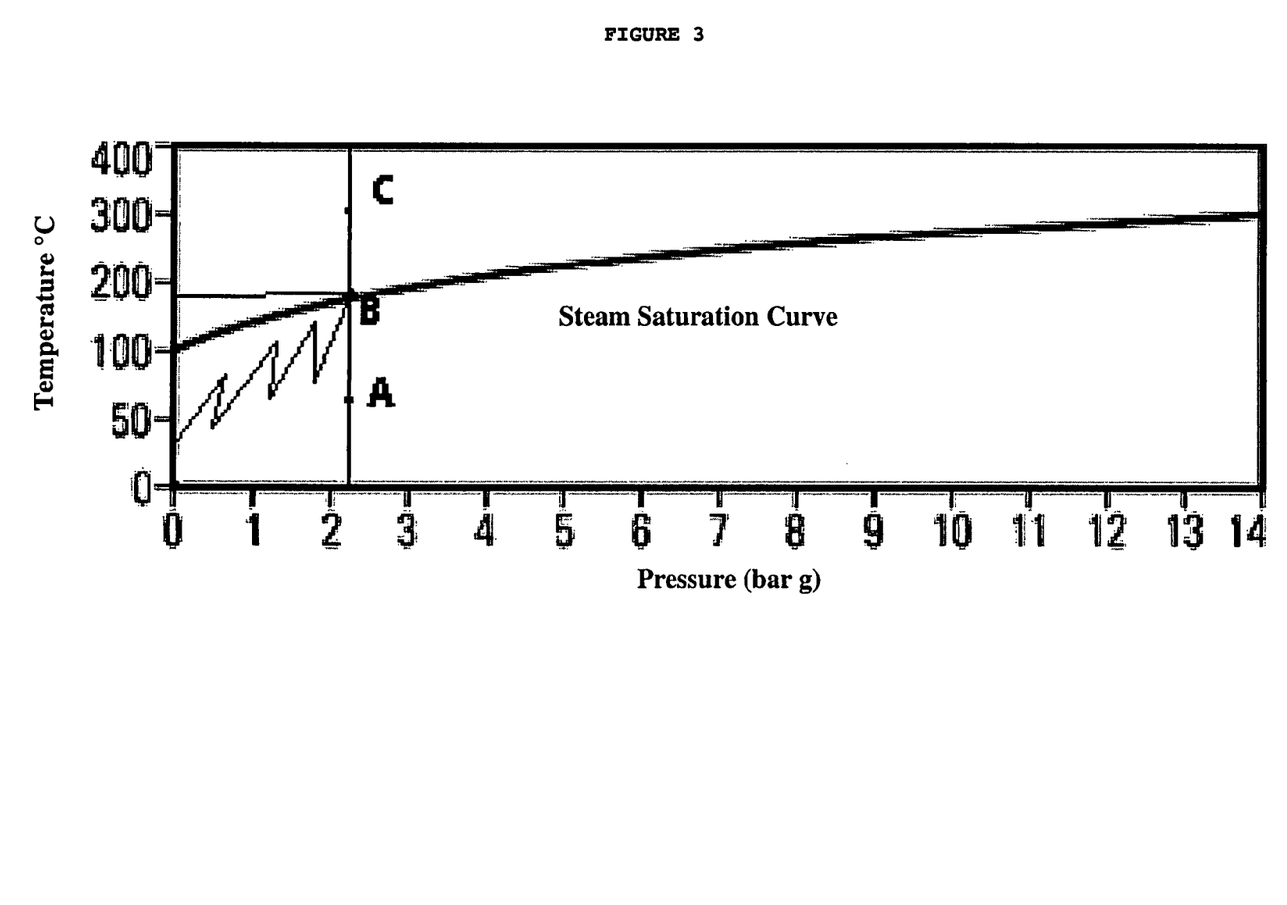
FIG. 3: shows an example of the operating curve of the Programmable Steam Trap apparatus (PST) during a sterilization process from the heating phase to the end of the sterilization process.

During the sterilization stage, the control system monitors the temperature and pressure and adjusts the temperature and/or pressure according to the saturation curve by controlling opening and closing of valves AV1 and AV2. The system can be run for 20 minutes, which is the minimum required time for sterilization. At this point in the sterilization process the following options are available:
1. If the temperature at TS1 is lower than $T_{sterilization}$ by more than −1° C. (point A in FIG. 3), there is still condensate in the system. AV2 is opened for several seconds to discharge all the condensate. The "heating stage" continues as AV1 is opened and the pressure in the vessel is maintained at $P_{sterilization}$.
2. If the temperature at TS1 is higher than $T_{sterilization}$ by more than 1° C. (point C in FIG. 3), the system contains superheated steam. AV2 is opened for several seconds in order to decrease the pressure and the temperature. At the same time the valve AV1 is closed.
3. If the temperature at TS1 is $T_{sterilization}$ ±0.5° C. (point B in FIG. 3), the system is operating on the steam saturation curve. In this scenario, the valves (AV1 and AV2) remain closed. As the sterilization progresses, if the pressure rises to over 1.14 bar gauge (~122.5° C.) AV2 is opened for several seconds. If the pressure decreases to below 1.06 bar gauge (~121.5° C.) AV2 remains closed. AV2 in this case is controlled according to the temperature at TS2 and AV1 is controlled by TS1. In this manner the operation curve of the sterilization process remains on or close to the steam saturation curve.

Alternatively, in one trial, the sterilization stage was conducted as follows:
1. When the pressure increases above the set point (e.g., 1.3 bar gauge), valve AV2 is opened for a minimal time (seconds) to reduce the system's pressure.
2. When the pressure decreases below the set point, AV1 is opened for a minimal time (seconds) to increase the system's pressure.

Thus, the system is stabilized according to the steam saturation curve with minor deviations.

The PST described above was tested using a stainless steel vessel (2.2 L). The actuated valve AV2 was placed 80 cm below the vessel separated by a ½" diameter pipe. The other valve AV1 was placed at the top of the vessel. The temperature sensors TS1 and TS2 were located in the vessel and the drain line respectively. The system was operated as described above and the results were compared to a common sterilization system.

Results

Figure 5:
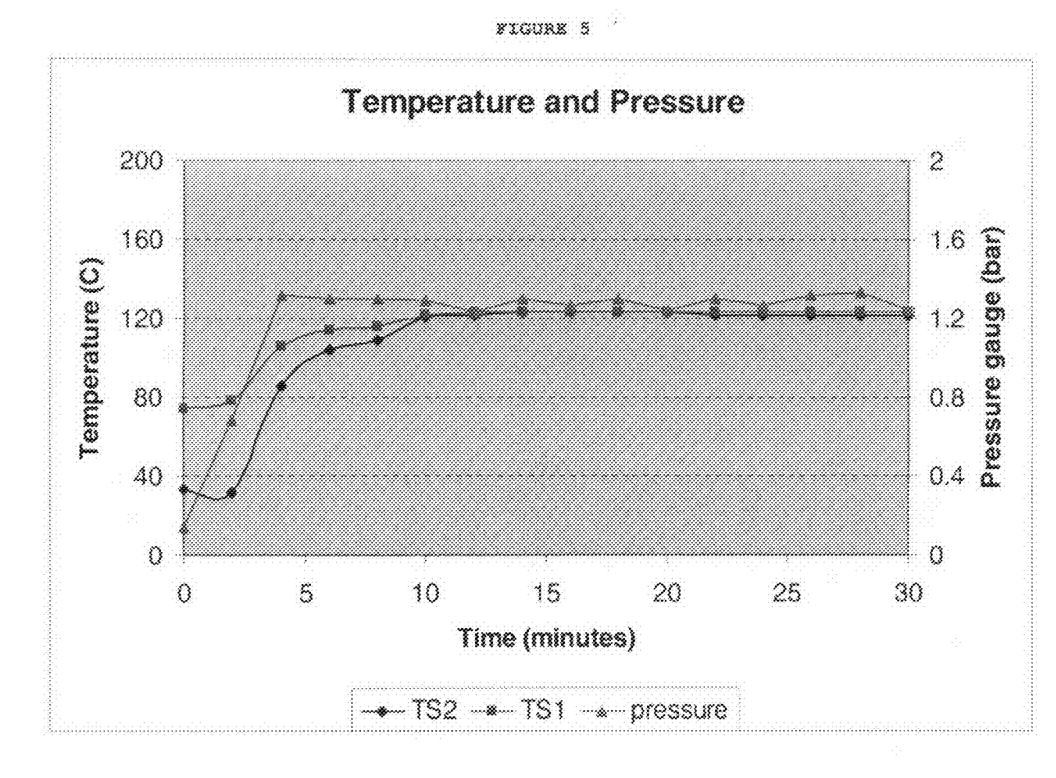
FIG. 5: shows the temperature and the pressure of the drain and the vessel during the sterilization cycle in Experiment 1. (temperature of the vessel is designated by TS1; temperature of the drain is designated by TS2)

The results of the experiment are summarized in Tables 1 and 2 and FIG. 5. Table 1 shows the ranges of system temperature and pressure during the sterilization cycle. Table 2 compares the performance of the Programmable steam trap (PST) system to a common sterilization system.

TABLE 1

Temperature and pressure values during the sterilization cycle.

|  | TS1 | TS2 | PS1 |
| --- | --- | --- | --- |
| Heating period - time to reach the setpoint (minutes) | 10 | 10 | 4 |
| Ranges of values during sterilization | 122-123° C. | 121-123° C. | 1.24-1.34 bar gauge |
| Average values during sterilization | 122.7° C. | 122.2° C. | 1.30 bar gauge |

TABLE 2

Comparison of the PST performance to a common sterilization system

|  | PST System | Common sterilization system |
| --- | --- | --- |
| Heating period - time to reach the setpoint (minutes) | 10 | 14 |
| Purified water volume consumed in one sterilization cycle (Liters) | 1.5 | 3.5 |
| System pressure ranges (bar gauge) | 1.2-1.4 | 2.0-2.9 |
| Maximum temperature reached(° C.) | 123 | 127 |
| System operation | Controlled according to pressure and temperature | Controlled according to temperature only |

Discussion

This experiment demonstrated the numerous advantages of the PST system over the common sterilization system:

1. Shorter sterilization time: Since the temperature and the pressure were kept constant, the sterilization period is no more than 20 minutes, the minimum time required for sterilization.
2. Pressure and temperature of the vessel were kept within a narrow range.
3. Less purified water/steam were used: The PST system saved more than 55% of water/steam during the sterilization as compared to the common sterilization system, resulting in energy savings.
4. Sterilization at the minimum allowed sterilization temperature (maximum of 123° C. compared to 127° C.): Sterilization at the minimum allowed sterilization temperature prevents or minimizes harm to the temperature sensitive equipment.

What is claimed is:

1. An apparatus for removing condensate, air, or non-condensable gas from vapor space in a vapor system while preventing the loss of vapor, the apparatus comprising:
   a first temperature sensor at a first position in the apparatus,
   a second temperature sensor, at a second position in the vapor system where condensate, air, or non-condensable gas collect, wherein the second position of the second temperature sensor is different from the first position of the first temperature sensor,
   a pressure sensor,
   an actuated valve in a position allowing for release of condensate, air, or non-condensable gas from the vapor space, and
   a control system which receives output from the first and second temperature sensors and from the pressure sensor and determines whether to open the actuated valve to release condensate, air or non-condensable gas from the vapor space based on temperature reading from the temperature sensors and the pressure reading from the pressure sensor;
   wherein the control system opens the actuated valve if it determines that condensate, air or non-condensable gas is present in the vapor system.

2. The apparatus of claim 1, wherein one or both of the temperature sensors are located within a thermowell pocket.

3. The apparatus of claim 2, wherein the thermowell pocket further comprises glycerol.

4. The apparatus of claim 1, wherein the actuated valve is positioned downstream from the first and the second temperature sensors.

5. The apparatus of claim 1, wherein the control system determines that condensate, air or non-condensable gas is present in the vapor system if the outputs from the temperature sensors and from the pressure sensor indicate that the vapor system is operating at below a vapor's saturation curve.

6. The apparatus of claim 1, wherein the control system is programmed to allow input of time intervals which represent a time delay between a signal to open or close the actuated valve and the opening or closing of the actuated valve.

7. The apparatus of claim 1, wherein the the vapor space and the actuated valve are separated by a distance of 20 meters or less.

8. The apparatus of claim 7, wherein the distance between the vapor space and the actuated valve is 80 cm or less.

9. The apparatus of claim 8, wherein the distance between the vapor space and the actuated valve is 5 cm or less.

10. The apparatus of claim 1, wherein the vapor space has a pressure of 1-5 bar.

11. The apparatus of claim 1, wherein the vapor system is a steam system.

12. A method for removing condensate, air, or non-condensable gas from vapor space in a vapor system while preventing the loss of vapor, the method comprising:
   a. measuring a temperature at a first region in the vapor system;
   b. measuring a temperature at a second region in the vapor system where condensate, air, or non-condensable gas collect, wherein the second region is different from the first region;
   c. measuring a pressure at a region in the vapor system;
   d. determining whether the temperatures and pressure obtained in steps a)-c) represents the presence of condensate, air, or non-condensable gas; and
   e. opening an actuated valve i the temperatures and pressure measured in steps a)-c) is determined to represent presence of condensate, air, or non-condensable gas.

13. The method of claim 12, wherein the determining step in d) is accomplished by comparing the temperatures and pressure obtained in steps a)-c) with a vapor's saturation curve.

14. The method of claim 13, wherein the actuated valve is opened if the temperatures and pressure obtained in steps a)-c) indicate that the vapor system is operating at below the vapor's saturation curve.

15. The method of claim 12, wherein the determining step in d) is automated.

16. The method of claim 15, wherein the automation is achieved by a control system.

17. The method of claim 16, wherein the control system is programmed to allow input of time intervals which represent a time delay between a signal to open or close the actuated valve and the opening or closing of the actuated valve.

18. The method of claim 17, wherein the actuated valve opening time interval is no more than 20 seconds.

19. The method of claim 18, wherein the actuated valve opening time interval is 1-10 seconds.

* * * * *

UNITED STATES PATENT AND TRADEMARK OFFICE
CERTIFICATE OF CORRECTION

| | | |
|---|---|---|
| PATENT NO. | : 8,739,808 B2 | Page 1 of 1 |
| APPLICATION NO. | : 12/800589 | |
| DATED | : June 3, 2014 | |
| INVENTOR(S) | : Aloni et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 958 days.

Signed and Sealed this
Seventeenth Day of February, 2015

Michelle K. Lee
*Deputy Director of the United States Patent and Trademark Office*